(12) United States Patent
Spaulding et al.

(10) Patent No.: US 8,834,856 B2
(45) Date of Patent: Sep. 16, 2014

(54) SYNERGISTIC PRESERVATIVE SYSTEM

(75) Inventors: Laura A. Spaulding, Wayne, NJ (US); Alissa R. Frontauria, Lodi, NJ (US); Vincent R. La Iaconna, Jersey City, NJ (US)

(73) Assignee: Eveready Battery Company, Inc., St. Louis, MO (US)

( * ) Notice: Subject to any disclaimer, the term of this patent is extended or adjusted under 35 U.S.C. 154(b) by 0 days.

(21) Appl. No.: 13/397,380

(22) Filed: Feb. 15, 2012

(65) Prior Publication Data

US 2012/0321572 A1   Dec. 20, 2012

Related U.S. Application Data

(60) Provisional application No. 61/443,040, filed on Feb. 15, 2011.

(51) Int. Cl.
*A61K 8/00*   (2006.01)
*A61K 8/27*   (2006.01)

(52) U.S. Cl.
USPC .......................................................... 424/59

(58) Field of Classification Search
CPC .... A61K 2800/524; A61K 8/27; A61Q 17/04
USPC .......................................................... 424/59
See application file for complete search history.

(56) References Cited

U.S. PATENT DOCUMENTS

| | | | |
|---|---|---|---|
| 7,854,940 B2 * | 12/2010 | Ciccognani et al. ........... | 424/404 |
| 2008/0226568 A1 | 9/2008 | Rozsa et al. | |
| 2010/0068160 A1 | 3/2010 | Springer et al. | |
| 2012/0012127 A1 * | 1/2012 | Rossi et al. .................... | 132/202 |

OTHER PUBLICATIONS

Newman, M.D. et al. "The safety of nanosized particles in titanium dioxide—and zinc oxide—based sunscreens." J. Am. Acad. Dermatol. 2009, 61 (4), 685-692.*

Australian Government: Dept of Health and Ageing: Therapeutic Goods Admin. "A review of the scientific literatureon the safety of nanoparticulate titanium dioxide or zinc oxide in sunscreens" Jul. 2009, pp. 1-32.*
International Search Report and Written Opinion Dated May 25, 2012 From Corresponding PCT Application No. PCT/US2012/25263.
"The Chemistry and Manufacture of Cosmetics, vol. 1- Science," 4th Edition, Edited by M.L. Schlossman, Chapter 19, Cosmetic Microbiology and Preservation, D.C. Steinberg p. 632-640.
CFR—Code of Federal Regulations Title 21, vol. 5, Revised as of Apr. 1, 2012, Title 21—Food and Drugs, Chapter I—Food and Drug Administration, Department of Health and Human Services, Subchapter D—Drugs for Human Use, Part 352 Sunscreen Drug Products for Over-the-Counter Human Use (Stayed Indefinately), pp. 1-12.
Health Canada (Health Products and Food Branch), "Draft: Guidance Document Sunscreen Monograph", dated Nov. 16, 2012, Version 2.0, pp. 1-22.
"Safety Assessment of Chlorphenesin as Used in Cosmetics", Final Report for Public Distribution, Release Date: Oct. 5, 2012, Panel Meeting Date: Sep. 10-11, 2012, pp. 1-14.
U.S. Department of Health and Human Services, Safety Alerts for Human Medical Products, "Mommy's Bliss Nipple Cream", Release date May 23, 2008, Page Last Updated Jun. 19, 2009, consisting of 1 page.
European Commission, Scientific Committee on Consumer Safety (SCCS), "Opinion on Zinc Oxide (nano form) COLIPA S 76" The SCCS adopted this opinion at its 16th plenary meeting of Sep. 18, 2012, Revision of Dec. 11, 2012 (SCCS/1489/12), pp. 1-112.
Australian Government, Department of Health and Ageing, OTC Medicines Section, Therapeutic Goods Administration, "A Review of the Scientific Literature of the Safety of Nanoparticulate Titanium Dioxide or Zinc Oxide in Sunscreens", Jul. 2009, pp. 1-32.

* cited by examiner

*Primary Examiner* — Sean Basquill
*Assistant Examiner* — Andrew S Rosenthal
(74) *Attorney, Agent, or Firm* — Energizer Personal Care, LLC

(57) ABSTRACT

A novel three-component synergistic preservative system has zinc oxide, a phenoxyethanol component, and caprylyl glycol. The preservative system provides sufficient preservative activity without the use of other preservatives such as parabens. It provides broad spectrum activity against yeast and molds, and remains effective long term.

9 Claims, 3 Drawing Sheets

SYNERGISTIC PRESERVATIVE SYSTEM

CROSS-REFERENCE TO RELATED APPLICATIONS

The present application claims priority to U.S. Provisional Patent Application No. 61/443,040, filed on Feb. 15, 2011.

BACKGROUND OF THE DISCLOSURE

1. Field of the Disclosure

The present disclosure relates to novel preservative systems. More particularly, the present disclosure relates to three-component preservative systems that exclude commonly used preservatives that may raise concerns with undesirable side effects.

2. Description of the Related Art

Effective preservative compositions must be both anti-microbial and anti-fungal. Most current preservative compositions contain some form of paraben, often in combination with phenols and quaternary compounds. However, some of the current paraben preservative systems are limited in their global acceptability. For example, some parabens are not allowed in either Europe or Japan, because they have shown estrogenic activity and other undesirable effects in various test models.

Other commonly used preservatives, such as formaldehyde donors, isothiazolinones, and ethanol, while being effective, can have safety/compatibility-related issues, for example, high irritation potential and incompatibility with avobenzone.

Accordingly, there is a need to develop a preservative system that exhibits strong preservative activity, without including preservatives, such as parabens, that exhibit undesirable side effects.

SUMMARY OF THE DISCLOSURE

The present disclosure provides a three-component synergistic preservative system including: zinc oxide; phenoxyethanol; a phenoxyethanol derivative, or a combination thereof; and caprylyl glycol. This preservative system provides strong preservative activity. This is surprising because zinc oxide has minimal preservative activity at low concentrations, phenoxyethanol has limited antifungal activity, and caprylyl glycol has no antifungal activity at all. The combination of these three components thus provides far greater preservative activity than one would normally expect.

Accordingly, in one embodiment, the present disclosure provides a preservative system comprising: zinc oxide; phenoxyethanol; a phenoxyethanol derivative, or a combination thereof; and caprylyl glycol. The ratio of the zinc oxide, the phenoxyethanol, phenoxyethanol derivative, or combination thereof, and the caprylyl glycol in the preservative system is between 0.5:0.2:0.2 and 20:5:2 by weight. The preservative system exhibits synergistic preservative activity.

In another embodiment, the present disclosure provides a composition comprising a preservative system. The preservative system comprises: zinc oxide, in an amount of 1.5 to 5.0 wt %, based on the total weight of the composition; phenoxyethanol, a phenoxyethanol derivative, or a combination thereof, in an amount of 0.2 to 5.0 wt %, based on the total weight of the composition; and caprylyl glycol, in an amount of 0.2 to 2.0 wt %, based on the total weight of the composition. The preservative system exhibits synergistic preservative activity.

DETAILED DESCRIPTION OF THE DISCLOSURE

Figure 1:
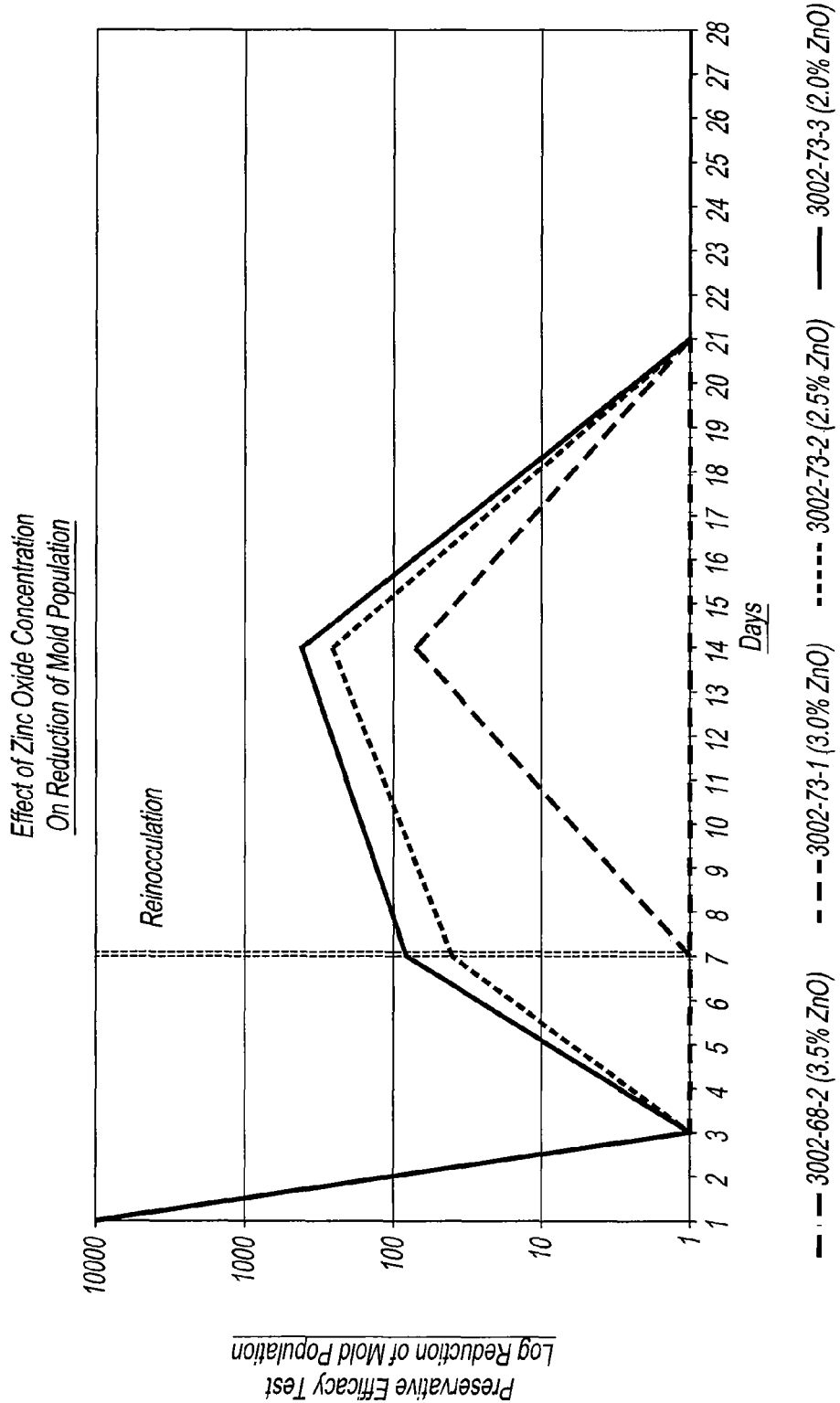
FIG. 1 shows the effect of zinc oxide concentration in the preservative system of the present disclosure on reduction in mold population.

The present disclosure provides a three-component preservative system that includes zinc oxide; phenoxyethanol, a phenoxyethanol derivative, or a combination thereof; and caprylyl glycol. Many prior art preservative systems included parabens such as methyl paraben and propyl paraben, which are very useful as antifungal agents. The present disclosure has surprisingly found that when the parabens are removed from the preservative system, the system still provides both antimicrobial and antifungal activity, even though the remaining compounds are not known for their antifungal activity. This is true even when the level of zinc oxide is low. Unexpectedly, the formula passed rigorous preservative challenge testing, as described in greater detail below.

Theoretically, the product should have failed the preservative challenge test, especially against fungi, since the zinc oxide level was too low to have any preservative effect, phenoxyethanol provides slight fungicidal activity, and caprylyl glycol has no fungicidal activity. The formula was prepared and tested multiple times, and all lots passed preservative challenge testing. The above-described preservative system can be used in any composition where preservative (i.e., countering the deteriorative effects of microorganisms in the composition) activity is desired, for example a sunscreen composition, or any other cosmetic composition.

The zinc oxide can be present in the composition at a level of 0.5% to 20%, 1.5% to 5%, or 2.5% to 3.5%, all based on the total weight of the composition. The zinc oxide can be uncoated, or coated, such as with silicas, silanes, methicones, dimethicones, or methicone/dimethicone copolymers. Zinc oxide is a weak antimicrobial and weak fungistat even at very high levels. In the paint industry, for example, zinc oxide is present in compositions at level of 30% by weight, which is the preferred use level to retard growth of mildew. Mildew growth can occur at 20% level of zinc oxide in paint compositions. At the weight ranges recited above for the compositions of the present disclosure, zinc oxide alone has almost no bactericidal or fungicidal properties. Very surprisingly, however, both coated and uncoated zinc oxide were effective in the 3-component preservative system of the present disclosure, even at very low levels of zinc oxide.

Phenoxyethanol, a phenoxyethanol derivative, or a combination thereof, can be present in an amount of 0.2% to 5%, or 0.5%-1%, based on the total weight of the composition. It is an oil soluble liquid that is an antimicrobial agent with very minor fungicidal activity.

Caprylyl glycol can be present in an amount of 0.2% to 2%, or 0.5% to 1%, based on the total weight of the composition. It is an oil soluble semi-solid, having antimicrobial properties and no fungicidal activity.

In one embodiment, the preservative system consists essentially of zinc oxide, phenoxyethanol, and caprylyl glycol, meaning that the preservative system, and/or the composition in which it is used, is free of any other components that exhibit preservative activity. In another embodiment, the preservative system consists of zinc oxide, phenoxyethanol, and caprylyl glycol.

The preservative system may also comprise zinc oxide, phenoxyethanol, and caprylyl glycol, if additional preservative activity is desired. Additional preservative components can be added to some embodiments of the preservative system of the present disclosure, but as the three components discussed above exhibit strong preservative activity on their own, adding additional components may be redundant and would make the resulting composition unnecessarily costly.

The preservative system of the present disclosure has several advantages over those currently available. It is free of parabens. Parabens are sometimes undesirable because they have exhibited estrogenic activity. It is also free of other preservatives, such as formaldehyde donors and isothiazolinones, which can cause skin irritation. The preservative system of the present disclosure also exhibits preservative activity over a broad spectrum, e.g. both antimicrobial and antifungal activity. It is able to kill all types of microorganisms, including fungi such as yeast and mold, and Gram-positive and Gram-negative bacteria. It is effective at low concentrations, which is advantageous in that it can be used at the lowest concentrations to meet preservative requirements, while also reducing chances of irritation and addressing other toxicity concerns. It has high water solubility, which is advantageous since most microorganisms grow in the water phase or at the water-oil interface. Preservatives should thus be in the water phase to function. The more water soluble and the less oil-soluble the preservative system is, the better it will function. The preservative system of the present disclosure is also effective over the anticipated shelf life of the compositions in which it is used. All of these features are available at low levels of zinc oxide, and with only the three components or ingredients discussed above. This saves on cost, and makes the preservative system easier to prepare.

The preservative system of the present disclosure is also stable under all temperature and pH conditions that it would encounter during the manufacture of the composition in which it is ultimately used. It is also colorless and odorless, and does not add color or odor to the composition, or react with other ingredients to form colors or odors. The preservative system of the present disclosure is compatible will all ingredients in the composition, and does not lose preservative activity in their presence. The preservative system should also function during the manufacturing and throughout the intended life of the cosmetic product, and be safe to use.

The term "preservation" as used in the present disclosure refers to the prevention or retardation of product deterioration due to microorganisms present in the product, from the time of manufacture until the product (such as a topical composition) is used up by the consumer. A "preservative" is an ingredient that reacts with, prevents, or retards the growth of microorganisms in the personal care product. Ideally, a single preservative would act equally well against all microorganisms, but it is extremely difficult to find such a compound. Preservatives that are active against bacteria are usually poor against fungi, and vice versa. Therefore, a preservative system, using two or more preservatives, is needed.

Preservative Efficacy Testing

The adequacy of a particular preservative system is established by conducting a Preservative Efficacy Test (PET), also known as challenge testing. The major purpose of performing PET is to determine if the product can withstand consumer contamination. Other uses include establishing the efficacy of the preservative and the ability to withstand contamination during manufacturing. The data below establishes the adequacy of the preservative system of the present disclosure.

For purposes of the present disclosure, a "synergistic effect" is noted when a combination of ingredients is able to reduce bacterial and fungi colony forming units (cfu) from "To Numerous To Count (TNTC)" which could be greater than 10,000 cfu/mL, to: <10 cfu/mL at Day 7 and 14 for bacteria with no increase in growth for the remaining test period, and <1000 cfu/mL at Day 7 and 14 for fungi with no increase in growth for the remaining test period. No increase in growth is defined "as not more than half a log unit higher than the previous value measured.

Reinoculation occurs on Day 7, after the count. Reinoculation of the bacteria and mold simulates post-sale conditions. For example, when a user applies a sunscreen, they will often use the product once, close the container in which it is held, then open the container again, which exposes the composition to additional bacteria and fungi.

The microorganisms used in the testing are as follows:
Bacterial Pool:

| Gram Negative Bacilli | |
|---|---|
| Pseudomonas aeruginosa | ATCC 9027 |
| Burkholderia cepacia | ATCC 25416 |
| Gram Positive Bacilli | |
| Staphylococcus aureus | ATCC 6538 |
| Gram Negative Enteric Bacilli | |
| Eschericia coli | ATCC 8739 |
| Klebsiella pneumonia | ATCC 13833 |

Fungi Pool:

| Yeast | |
|---|---|
| Candida albicans | ATCC 10231 |
| Mold | |
| Penicillium chrysogenum | ATCC 10106 |
| Aspergillus niger | ATCC 15404 |

The PET consists of challenging a non-contaminated product with prescribed inoculums of suitable microorganisms according to standardized procedures, and storing the inoculated product at a prescribed temperature. Using serial dilutions and plate counts, the number of organisms surviving in the test products is determined at specified intervals. Products meeting the specified criteria will be considered adequately preserved for manufacture and consumer use. Products not meeting the criteria will be considered inadequately preserved. The various studies below validate the synergistic effect of the preservative system of the present disclosure, at very low use levels of zinc oxide, phenoxyethanol and caprylyl glycol.

ABBREVIATION KEY

ZnO—Zinc Oxide
PhE—Phenoxyethanol
CapG—Caprylyl Glycol
PP—Propyl Paraben
MP—Methyl Paraben
A—Adequate
I—Inadequate
Ma—Marginal, result at the borderline, indicating weak effectiveness
M—Month Section 1

Confirmation of Preservative System Effectiveness at Initial Time Point

The formulation base was an oil-in-water emulsion containing typical emollients, emulsifiers, thickeners, film formers, and sunscreen actives. In general, oil and water phases are heated separately to high temperatures with the novel preservative system already added, then combined with homogenization, and then cooled to room temperature. In some emulsions, a cold process may be used, and there may be more than two phases.

As shown in Table I, three different lots prepared on different dates and microbiologically tested on different dates unexpectedly and successfully passed the PET. Knowing that the first lot 3002-38 passed the PET, we wanted to have positive and negative control batches for the second round of evaluation to verify PET accuracy. The negative control lot 3002-63-3, which is missing phenoxyethanol, had CFU that were TNTC on Day 7 and Day 14. The data in Table I confirms the reproducibility of the novel preservative system consisting of zinc oxide, phenoxyethanol, and caprylyl glycol. Also, the data in Table I shows that when the additional preservatives propylparaben and methylparaben are added, the resulting preservative system still passes testing.

Section 2

Confirmation of Synergistic Preservative System Effectiveness after Storage at Elevated Temperature It is equally important that the preservative system remain effective during shelf-life storage, and that the preservative system does not deteriorate or cause the product to deteriorate. Therefore, formulated products were stored at 40° C. for

TABLE I

Multiple Lot Confirmation of Synergistic Preservative System Effectiveness

| Lot # | PET Start Date | ZnO % | PhE % | CapG % | PP % | MP % | PET* Result |
|---|---|---|---|---|---|---|---|
| 3002-38 | Dec. 05, 2008 | 3.0 | 1.0 | 1.0 | — | — | A |
| 3002-63-2 | Feb. 09, 2009 | 3.0 | 1.0 | 1.0 | — | — | A |
| 3002-73-1 | Feb. 23, 2009 | 3.0 | 1.0 | 1.0 | — | — | A |
| Controls | | | | | | | |
| 3002-63-1 | Feb. 09, 2009 | 3.0 | 1.0 | 1.0 | 0.15 | 0.25 | A |
| 3002-63-3 | Feb. 09, 2009 | 3.0 | — | 1.0 | — | — | I |

*Procedure for PET specifies re-inoculation of sample on Day 7.

In an effort to fully establish the uniqueness of the synergistic preservative system, another series of sunscreen oil-in-water emulsions were prepared to determine the effectiveness of various combinations of just two of the ingredients in the 3-component preservative system. Results shown in Table II proved that only the unique to combination of zinc oxide, phenoxyethanol, and caprylyl glycol was effective in preserving the product.

one and three months and then subjected to PET. The data in Table III and Table IV confirmed the long term effectiveness of the 3-component preservative system. All batches passed color, odor, and appearance at initial, and at the elevated storage condition of 40° C. for up to three months. In Table III, control batch 3002-63-1 included 0.15 wt % of methyl paraben, and 0.25 wt % of propyl paraben.

TABLE II

Establishing Uniqueness of 3-Component Synergistic Preservative System

| Lot # | PET Start Date | ZnO % | PhE % | CapG % | PP % | MP % | PET* Result |
|---|---|---|---|---|---|---|---|
| 3002-68-2 | Feb. 16, 2009 | 3.5 | 1.0 | 1.0 | — | — | A |
| Controls | | | | | | | |
| 3002-68-3 | Feb. 16, 2009 | 3.5 | — | 1.0 | — | — | I |
| 3002-70-2 | Feb. 16, 2009 | 3.5 | 1.0 | — | — | — | I |
| 3002-70-3 | Feb. 16, 2009 | 3.5 | — | — | — | — | I |

*Procedure for PET specifies re-inoculation of sample on Day 7.

TABLE III

Multiple Lot Confirmation of Synergistic Preservative System Effectiveness After Long Term Storage Stability at Elevated Conditions

| Lot # | PET Start Date | ZnO % | PhE % | CapG % | Initial PET* | 1M 40° C. PET* | 3M 40° C. PET* |
|---|---|---|---|---|---|---|---|
| 3002-63-2 | Feb. 09, 2009 | 3.0 | 1.0 | 1.0 | A | A | A |
| 3002-73-1 | Feb. 23, 2009 | 3.0 | 1.0 | 1.0 | A | A | A |

TABLE III-continued

Multiple Lot Confirmation of Synergistic Preservative System Effectiveness After Long Term Storage Stability at Elevated Conditions

|  | PET Start Date | ZnO % | PhE % | CapG % | Initial PET* | 1M 40° C. PET* | 3M 40° C. PET* |
|---|---|---|---|---|---|---|---|
| Controls | | | | | | | |
| 3002-63-1 | Feb. 09, 2009 | 3.0 | 1.0 | 1.0 | A | A | A |
| 3002-63-3 | Feb. 09, 2009 | 3.0 | — | 1.0 | I | I | I |

*Procedure for PET specifies re-inoculation of sample on Day 7.

TABLE IV

Confirmation of Synergistic Preservative System Effectiveness After Long Term Storage Stability at Elevated Conditions

|  | PET Start Date | ZnO % | PhE % | CapG % | Initial PET* | 1M 40° C. PET* | 3M 40° C. PET* |
|---|---|---|---|---|---|---|---|
| Lot # | | | | | | | |
| 3002-68-2 | Feb. 16, 2009 | 3.5 | 1.0 | 1.0 | A | A | A |
| Controls | | | | | | | |
| 3002-68-3 | Feb. 16, 2009 | 3.5 | — | 1.0 | I | I | Ma |
| 3002-70-2 | Feb. 16, 2009 | 3.5 | 1.0 | — | I | I | I |
| 3002-70-3 | Feb. 16, 2009 | 3.5 | — | — | I | I | I |

*Procedure for PET specifies re-inoculation of sample on Day 7.

Section 3

Establishing Range of Zinc Oxide for the Novel Synergistic Preservative System

The zinc oxide concentration in the oil-in-water emulsion system was varied from 2.0-3.5%, and studied over time to approximate a lower limit. As shown in Table V, the PET end results were adequate though out the long term stability studies for all the various levels of ZnO. However, differences in ZnO efficiency were noted among the concentration levels when examining the actual number of CFU during the course of the PET studies with the initial time point samples as illustrated in FIG. 1.

Section 4

Figure 2:
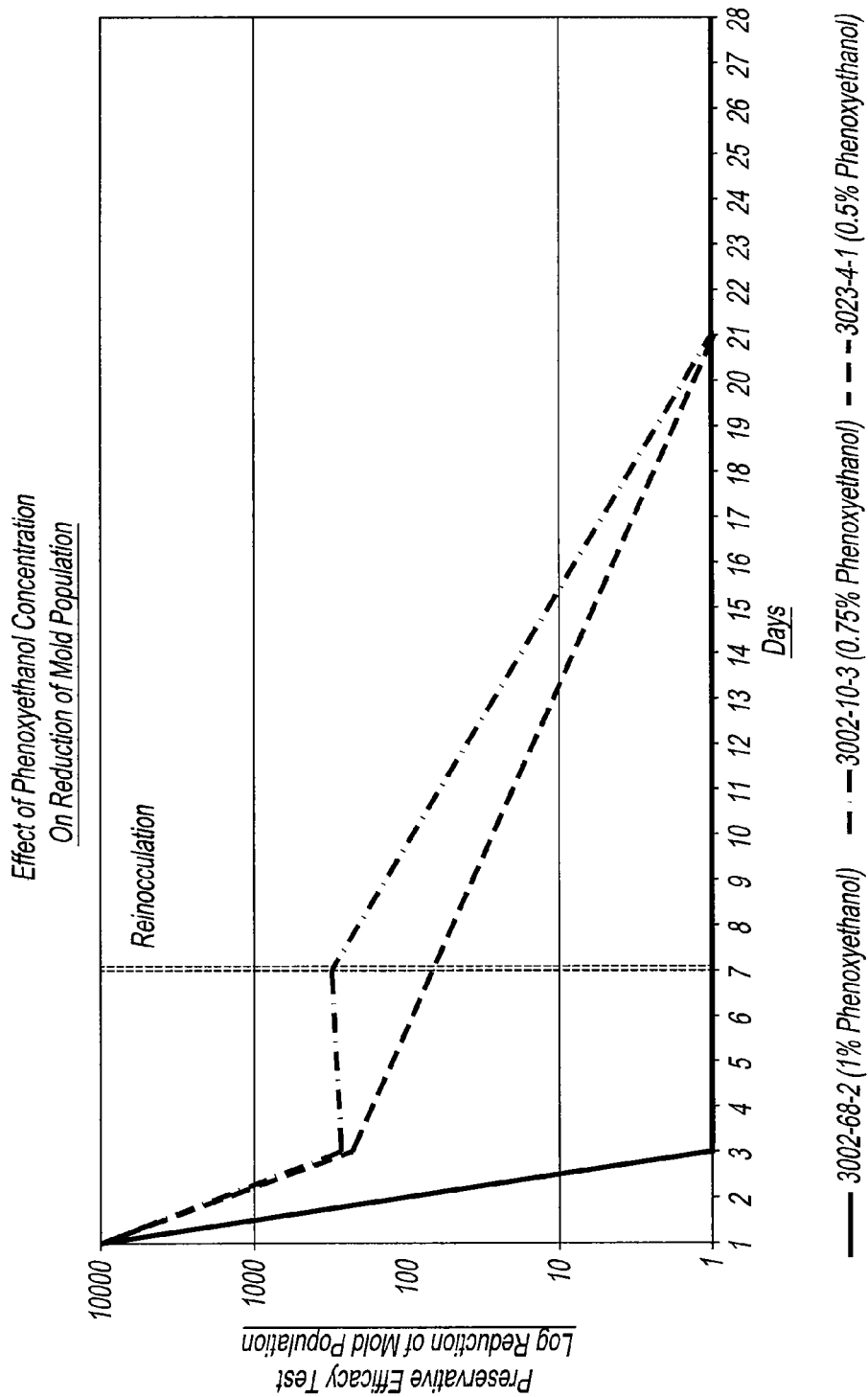
FIG. 2 shows the effect of phenoxyethanol concentration in the preservative system of the present disclosure on reduction in mold population.

Establishing Range of Phenoxyethanol for the Novel Synergistic Preservative System The phenoxyethanol concentration in the oil-in-water emulsion system was varied from 0.5% to 1.0%. As shown in Table VI, the PET marginal results for the lower levels of phenoxyethanol suggested that the overall preservative system was weak and there was a possibility of failures in the future. However, FIG. 2 depicts the differences in effectiveness of the various levels of phenoxyethanol, and shows that even if the preservative activity results were weak at the Day 7 stage, in the long term, each of the three samples tested, at varying weights of phenoxyethanol, showed adequate preservative activity at Day 28.

TABLE V

Effect of Zinc Oxide Concentration in the Synergistic Preservative System

| Lot # | PET Start Date | ZnO % | PhE % | CapG % | Initial PET* | 1M 40° C. PET* | 3M 40° C. PET* |
|---|---|---|---|---|---|---|---|
| 3002-68-2 | Feb. 09, 2009 | 3.5 | 1.0 | 1.0 | A | A | A |
| 3002-73-1 | Feb. 23, 2009 | 3.0 | 1.0 | 1.0 | A | A | A |
| 3002-73-2 | Feb. 23, 2009 | 2.5 | 1.0 | 1.0 | A | A | A |
| 3002-73-3 | Feb. 23, 2009 | 2.0 | 1.0 | 1.0 | A | A | A |

*Procedure for PET specifies re-inoculation of sample on Day 7.

TABLE VI

Effect of Phenoxyethanol Concentration
in the Synergistic Preservative System

| Lot # | PET Test Date | ZnO % | PhE % | CapG % | Initial PET* |
|---|---|---|---|---|---|
| 3002-68-2 | Feb. 09, 2009 | 3.5 | 1.0 | 1.0 | A |
| 3002-100-3 | May 04, 2009 | 3.5 | 0.75 | 1.0 | Ma |
| 3023-4-1 | May 04, 2009 | 3.5 | 0.5 | 1.0 | Ma |

*Procedure for PET specifies re-inoculation of sample on Day 7.

Section 5

Figure 3:
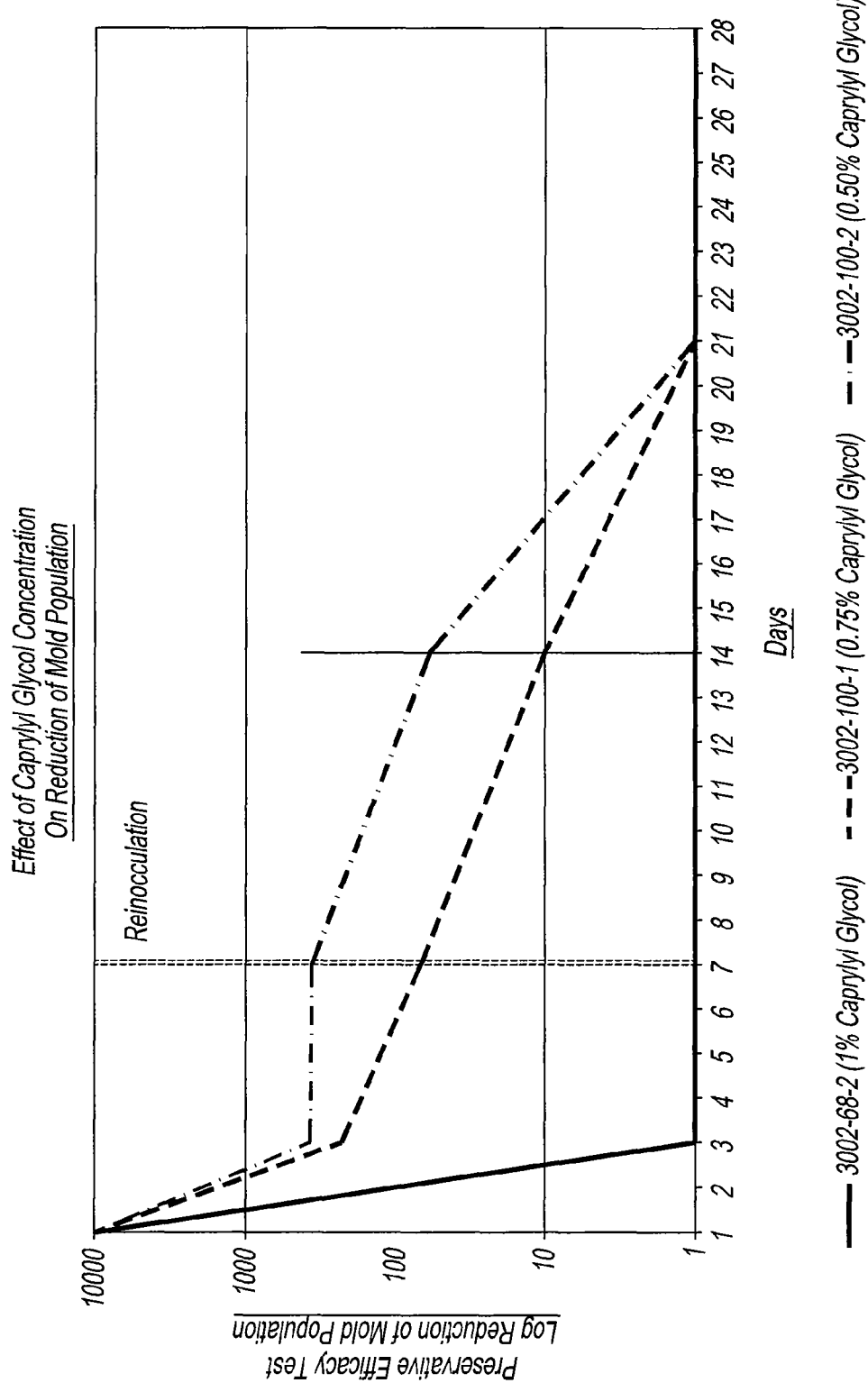
FIG. 3 shows the effect of caprylyl glycol concentration in the preservative system of the present disclosure on mold population.

Establishing Range of Caprylyl Glycol for the Novel Synergistic Preservative System The caprylyl glycol concentration in the oil-in-water emulsion system was varied from 0.5% to 1.0% to help establish a lower limit. As shown in Table VII, the PET results were adequate for the 1% and 0.75% level of caprylyl glycol. It should be noted that at the 0.75% level the number of CFU was just above the marginal point suggesting a relatively weaker preservative system. The PET marginal results for the 0.5% level of caprylyl glycol suggested that this particular preservative system was less effective and there was a possibility of failures in the future. Similarly with phenoxyethanol, FIG. 3 depicts the differences in effectiveness of the various levels of caprylyl glycol, and shows that even if the preservative activity results were weak at the Day 7 stage, in the long term, each of the three samples tested, at varying weights of phenoxyethanol, showed adequate preservative activity at Day 28.

TABLE VII

Effect of Caprylyl Glycol Concentration
in the Synergistic Preservative System

| Lot # | PET Test Date | ZnO % | PhE % | CapG % | Initial PET* |
|---|---|---|---|---|---|
| 3002-68-2 | Feb. 09, 2009 | 3.5 | 1.0 | 1.0 | A |
| 3002-100-1 | May 04, 2009 | 3.5 | 1.0 | 0.75 | A |
| 3023-100-2 | May 04, 2009 | 3.5 | 1.0 | 0.5 | Ma |

*Procedure for PET specifies re-inoculation of sample on Day 7.

Section 6

Influence of Emulsion Type on Novel Synergistic Preservative System

The 3-component synergistic preservative system adequately passed the PET when added to the oil-in-water emulsion. The next step was to verify its effectiveness in a water-in-oil emulsion system. Since water is the internal phase and present at much lower concentration, one would expect that less preservative would be needed to is adequately pass the PET. The data provided in Table VIII verified the capability of the 3-component synergistic system to adequately preserve a water-in-oil emulsion, even at lower concentration of phenoxyethanol and caprylyl glycol.

TABLE VIII

Synergistic Preservative System in Water-in-Oil Emulsion

| Lot # | PET Test Date | ZnO % | PhE % | CapG % | Initial PET* |
|---|---|---|---|---|---|
| 3023-9 | May 18, 2009 | 3.0 | 1.0 | 1.0 | A |
| 3023-10 | May 18, 2009 | 3.0 | 0.5 | 0.5 | A |

Section 7

Effect of Coated Zinc Oxide in Novel Synergistic Preservative System

Zinc oxide is available in coated and uncoated forms for use in cosmetic products. Therefore, it was important to determine the effectiveness of the coated zinc oxide in the synergistic preservative system. Zinc oxide with a triethoxycaprylsilane (TEC) surface treatment, and zinc oxide with a silica and methicone/dimethicone copolymer (SMD) treatment replaced the uncoated zinc oxide. The two modified preservative systems were incorporated into an oil-in-water emulsion formulation. It would ordinarily be suspected that coating zinc oxide would eliminate any preservative activity that it exhibited. Very surprisingly, the preservative systems containing the coated zinc oxides adequately passed the PET as shown in Table IX.

TABLE IX

Synergistic Preservative System Containing Coated Zinc Oxide

| Lot # | Coating | PET Test Date | ZnO % | PhE % | CapG % | Initial PET* |
|---|---|---|---|---|---|---|
| 3023-12-1 | TEC | May 18, 2009 | 3.5 | 1.0 | 1.0 | A |
| 3023-12-2 | SMD | May 18, 2009 | 3.5 | 1.0 | 1.0 | A |

CONCLUSION

The discovery of a novel 3-component synergistic preservative system comprising zinc oxide, phenoxyethanol, and caprylyl glycol allows for products containing water to be formulated without the use of parabens. The 3-component system at low concentrations provided broad spectrum activity against yeast and molds. The synergistic preservative system remained effective long term as indicated by the adequate results from the 3 month 40° C. stability samples. The emulsions retained their integrity, indicating the compatibility of the preservative system with typical cosmetic formulation ingredients.

While the instant disclosure has been described with reference to one or more particular embodiments, it will be understood by those skilled in the art that various changes may be made and equivalents may be substituted for elements thereof without departing from the scope thereof. In addition, many modifications may be made to adapt a particular situation or material to the teachings of the disclosure without departing from the scope thereof. Therefore, it is intended that the disclosure not be limited to the particular embodiment(s) disclosed as the best mode contemplated for carrying out this disclosure.

The invention claimed is:

1. A preservative system, comprising:
   zinc oxide;
   a phenoxyethanol component selected from the group consisting of phenoxyethanol, a phenoxyethanol derivative, and a combination thereof; and
   caprylyl glycol,
   wherein the ratio of said zinc oxide, said phenoxyethanol component, and said caprylyl glycol in the preservative system is between 2.5:0.5:0.5 and 3.5:1:1 by weight, and
   wherein the preservative system exhibits synergistic anti-bacterial activity, synergistic anti-fungal activity, or a combination thereof.

2. The preservative system of claim 1, wherein the preservative system is free of parabens, formaldehyde donors, and isothiazolinones.

3. The preservative system of claim 1, consisting essentially of said zinc oxide, said phenoxyethanol component, and said caprylyl glycol.

4. The preservative system of claim 1, consisting of said zinc oxide, said phenoxyethanol component, and said caprylyl glycol.

5. A composition comprising a preservative system, said preservative system comprising:
    zinc oxide, in an amount of 1.5 to 5.0 wt %, based on the total weight of the composition;
    a phenoxyethanol component selected from the group consisting of phenoxyethanol, a phenoxyethanol derivative, and a combination thereof, in an amount of 0.75 to 1.0 wt %, based on the total weight of the composition; and
    caprylyl glycol, in an amount of 0.75 to 1.0 wt %, based on the total weight of the composition,
    wherein the preservative system exhibits synergistic preservative activity.

6. The composition of claim 5, wherein
    said zinc oxide is present in an amount of 2.5 to 3.5 wt %, based on the total weight of the composition.

7. The composition of claim 5, further comprising a sunscreen active.

8. The composition of claim 5, wherein said preservative system consists essentially of said zinc oxide, said phenoxyethanol component, and said caprylyl glycol.

9. A composition comprising a preservative system, the preservative system comprising:
    zinc oxide, in an amount of 2.5 to 3.5 wt. %, based on the total weight of the composition;
    a phenoxyethanol component selected from the group consisting of phenoxyethanol, a phenoxyethanol derivative, and a combination thereof, in an amount of 0.75 to 1.0 wt %, based on the total weight of the composition; and
    caprylyl glycol, in an amount of 0.75 to 1.0 wt %, based on the total weight of the composition,
    wherein the ratio of said zinc oxide, said phenoxyethanol component, and said caprylyl glycol in the preservative system is between 2.5:0.5:0.5 and 3.5:1:1 by weight, and
    wherein the preservative system exhibits synergistic anti-bacterial activity, synergistic anti-fungal activity, or a combination thereof.

* * * * *